United States Patent [19]

Zimmerman

[11] Patent Number: 5,386,111
[45] Date of Patent: Jan. 31, 1995

[54] OPTICAL DETECTION OF WATER DROPLETS USING LIGHT REFRACTION WITH A MASK TO PREVENT DETECTION OF UNREFRACTED LIGHT

[76] Inventor: H. Allen Zimmerman, 6490 S.W. 154th Pl., Beaverton, Oreg. 97007

[21] Appl. No.: 134,407

[22] Filed: Oct. 8, 1993

[51] Int. Cl.$^6$ ............................................. H01J 5/16
[52] U.S. Cl. ................................ 250/227.25; 318/444
[58] Field of Search ............. 250/227.25; 318/483, 318/444, DIG. 2

[56] References Cited

U.S. PATENT DOCUMENTS

| | | | |
|---|---|---|---|
| 3,487,492 | 1/1970 | Bischoff | 15/250 |
| 3,649,898 | 3/1972 | Inoue | 318/483 |
| 3,826,979 | 7/1974 | Steinmann | 324/61 R |
| 3,864,659 | 2/1975 | Furuuchi et al. | 338/35 |
| 4,010,383 | 3/1977 | Grassmann | 307/118 |
| 4,127,763 | 11/1978 | Roselli | 219/203 |
| 4,131,834 | 12/1978 | Blaszkowaski | 318/483 |
| 4,317,073 | 2/1982 | Blaszkowski | 318/483 |
| 4,355,271 | 10/1982 | Noack | 318/480 |
| 4,463,294 | 7/1984 | Gibson | 318/313 |
| 4,481,450 | 11/1984 | Watanabe et al. | 318/444 |
| 4,499,410 | 2/1985 | Iacoponi et al. | 318/444 |
| 4,554,493 | 11/1985 | Armstrong | 318/444 |
| 4,589,771 | 5/1986 | Watanabe et al. | 356/38 |
| 4,595,866 | 6/1986 | Fukatsu et al. | 318/444 |
| 4,620,141 | 10/1986 | McCumber et al. | 318/483 |
| 4,636,698 | 1/1987 | Leclercq | 318/443 |
| 4,665,351 | 5/1987 | Nyberg | 318/483 |
| 4,676,638 | 6/1987 | Yasuda | 356/237 |
| 4,810,022 | 3/1989 | Takagi et al. | 296/180.5 |
| 4,859,867 | 8/1989 | Larson et al. | |
| 4,867,561 | 9/1989 | Fujii et al. | 356/237 |
| 4,916,374 | 4/1990 | Schierbeek et al. | 318/483 |
| 4,956,591 | 9/1990 | Schierbeek et al. | 318/483 |
| 4,960,996 | 10/1990 | Hochstein | 250/349 |
| 4,970,122 | 11/1990 | Palanisamy | 428/432 |
| 5,015,931 | 5/1991 | Muller | 318/483 |
| 5,059,877 | 10/1991 | Teder | 318/444 |
| 5,306,992 | 4/1994 | Dröge | 318/483 |

FOREIGN PATENT DOCUMENTS 57-186556 2/1983 Japan .

OTHER PUBLICATIONS

"Tech Briefs", Automotive Engineering, Aug. 1991, p. 44.

Primary Examiner—David C. Nelms
Assistant Examiner—Steven L. Nichols
Attorney, Agent, or Firm—Klarquist Sparkman Campbell Leigh & Whinston

[57] ABSTRACT

An optical detection system for detecting rain or other water droplets on the outer surface of a window and fog on the inner surface with a single photo-detector. The invention measures the accumulation of water droplets on the window by light refraction of a first light beam with droplets to redirect a first light beam to the photo-detector. A masking device prevents light from reaching the photo-detector directly without refraction. As a result the rain measurement output signal of the photo-detector increases with an increasing accumulation of water droplets on the window. The fog accumulation is measured by a second light beam reflected off the inner surface of the window to the photo-detector so that the output signal of the photo-detector decreases with increasing amounts of fog since fog scatters the light to reduce the amount of light reflected to the photo-detector. A third light source is focused directly on the photo-detector to bias it into an operating point of high sensitivity to infrared light and is connected in a negative feedback circuit from the output of the photo-detector amplifier. The photo-detector output is connected to a narrowband amplifier that is tuned to the frequency of an oscillator which pulses the first and second light sources at different times. As a result of this negative feedback, changes in the output signal due to external factors are cancelled so they do not produce errors.

20 Claims, 4 Drawing Sheets

OPTICAL DETECTION OF WATER DROPLETS USING LIGHT REFRACTION WITH A MASK TO PREVENT DETECTION OF UNREFRACTED LIGHT

The subject matter of the present invention relates generally to optical detection of water and in particular to optical detection of water droplets on a window, such as the windshield of an automobile or other vehicle using light refraction. A light beam is transmitted through the water droplets which refract the light beam to a photo-detector which produces an electrical measurement signal at the output of the photo-detector corresponding to the amount of water accumulation on the window. The apparatus and method of the present invention is especially useful for detecting moisture, including rain drops and fog or other precipitation on the windshield of automobiles or other vehicles in order to operate windshield wipers, heaters, fans and other devices for removing such rain and fog to improve the visibility through such windshield or for operating other devices such as motors for closing convertible tops, sunroofs, or other windows in the event of rain when the vehicle is left unattended.

BACKGROUND OF THE INVENTION

It has previously been proposed in U.S. Pat. No. 4,131,834 to Blaszkowski, issued Dec. 26, 1978, to provide moisture detectors based upon measuring changes in electrical conductivity between spaced electrodes which sense rain when the gap between such electrodes is bridged by the rainwater. However, the amount of conductivity varies with atmospheric contaminants in the water as well as corrosion and wear of the electrical contacts forming the electrodes. Therefore such moisture detectors do not provide accurate measurement of the amount of moisture present.

In addition, moisture detectors have been proposed for detecting moisture based on measuring the changing capacitance in the gap between spaced electrodes due to changes in the dielectric material of such gap, such as when water is present. However, such a moisture detector suffers from poor sensitivity due to the proximity effects of moving wiper blades on such capacitance and from interfering electrical fields from power lines and other sources.

It has also been proposed to detect moisture by sensing the sound created by infringing droplets but this is inaccurate and is unable to detect light mists or fog accumulations. Similarly, moisture detectors based upon measurement of the mass changes due to the presence of water droplets are insensitive to light mist or fog.

Some optical detectors have sensed moisture based upon the interruption of light beam by the water droplets. However, these detectors also are insensitive to gradual accumulations of moisture as mist or fog. Also, windshield wipers interrupt the light beam and require gating mechanisms to disable the light detector during wiper sweeps so they are somewhat impractical.

It is believed that moisture detectors which sense water droplets by light refraction within the droplets are a substantial improvement over these moisture detectors. However, previously optical detectors which detect raindrops based upon light refraction have suffered from several disadvantages, including small detecting area, low sensitivity, error signals due to ambient light, and dependence upon long-term stability of light sources and photo-detectors whose characteristics change significantly with temperature, aging, operating point, and supply voltage variations.

The optical detection method and apparatus of the present invention overcomes these problems using a first light beam transmitted through a large area of the window and by employing a mask which prevents the first light beam from directly reaching the photo-detector unless such light beam is refracted by water droplets on the outer surface of the windshield. As a result, the output signal of the photo-detector indicating the presence of water droplets is zero when no droplets are present and increases in amplitude with the size and amount of water droplets present on the windshield of the vehicle or other window for a more accurate and more sensitive measurement of the accumulation of rain on such window.

A second light source may be provided for measuring fog by reflecting a second light beam off the inner surface of the window to the photo-detector in order to detect fog on such inner surface. As a result of diffusion of the second light beam by the fog less light is reflected off of the window to the photo-detector so that the fog measurement signal decreases in amplitude with increasing amounts of fog. The output signal of the photo-detector for measuring the accumulation of fog is distinguished from that for measuring the accumulation of rain by operating the two light sources at different times such as by electronically switching the inputs of two current amplifiers driving such light sources in an alternating manner to the output of a single oscillator. A third light source directly radiates light upon the photo-detector to bias it to the proper operating point. A narrowband amplifier tuned to the oscillator frequency is connected to the output of the photo-detector transistor to amplify the rain and fog measurement signals. The output of such amplifier is connected through a negative feedback circuit to the third light source to cancel gain changes produced by changes in ambient light, temperature changes and aging of the light source and photo-transistor, and power supply variations.

It has been previously proposed in U.S. Pat. No. 5,059,877 to Teder, issued Oct. 22, 1991, to operate a windshield wiper on an automobile automatically by the optical detection of water droplets on the windshield using light reflection from the outer surface of the windshield. An accumulation of raindrops on such outer surface scatters or diffuses the light beam and reduces the output signal of the photo-detector with increases in raindrop accumulation. The photo-detector is a photo-transistor which is coupled to the windshield by a light pipe of small diameter which greatly reduces the measured area of the windshield to less than approximately 1 sq. cm. This reduces the sensitivity of measurement, especially to a small accumulation of raindrops. The optical detector system of the present invention solves these problems by using light refraction with a masking device in front of the photo-detector and a wider light beam which covers a much larger area of the windshield, over 31 sq. cm. This larger measurement area greatly improves the accuracy of measurement of the amount of accumulated rainfall. Also, the present invention operates in a more efficient manner by refracting the light beam with the water droplets to redirect it toward the photo-detector which is shielded from direct radiation of such light beam by the masking device. As a result the output signal of the photo-detector increases with an increase in the amount of raindrops thereby improving its sensitivity. In addition, the Teder rain measurement system is more sensitive to changes in ambient light levels and therefore requires that a compensation circuit sample and store the ambient light level signals for subtraction from the measurement signal. Also, high ambient light levels including bright sunlight or at night when the headlights of an approaching car strike the windshield at a light intensity greater than predetermined limits cause the raindrop detection and wiper operation process to be suspended temporarily. This ambient light problem is avoided in the optical detector of the present invention by employing oscillator pulsed light sources, a narrowband amplifier at the output of the photo-detector tuned to the oscillator frequency and negative feedback from the output of such amplifier through a bias light source directed at the photo-detector.

U.S. Pat. No. 4,867,561 to Fujii et al., issued Sep. 19, 1989, also shows a similar optical detector for detecting rain by light reflection from the windshield in a detection area of extremely small size of less than 2 sq. cm. The photo-detector is two-dimensional array of photo-electric transducer elements mounted within an optical system housing supported beneath the dashboard closely adjacent the windshield. This optical detector employs light reflection for sensing raindrops on the outer surface of the windshield so that the presence of the raindrops reduces the amount of light which is reflected to the photo-detector and thereby reduces the output signal of such photo-detector. As a result the Fujii detector system has limited sensitivity and reduced accuracy compared to that of the present invention. Ambient light level changes are also a problem with this detector. Thus the ambient light level is measured and used to reduce the threshold levels of the comparators in the detection circuit for measuring rain and fog in an attempt to reduce inaccuracies due to change in the ambient light level. Also no measurements may be made if excessive ambient light is present such as bright sunlight.

A similar teaching is also shown in U.S. Pat. No. 4,595,866 to Fukatsu et al., issued Jun. 17, 1986, which relates to an optical detector for detecting rain on the windshield by the transmission of light from an external light source outside the windshield to a photo-detector within the automobile. The light beam is transmitted directly to the photo-detector, so that the output signal of the photo-detector is reduced when raindrops accumulate on the outer surface of the windshield because they refract the light beam away from such photo-detector. The present invention differs by providing a mask in front of the photo-detector to prevent light from being transmitted directly from the light source to the photo-detector and refracting a portion of the light beam with the detected raindrops to the photo-detector. As a result the output signal of the photo-detector increases with increasing amounts of raindrops on the windshield. The light detector of Fukatsu et al. consists of a plurality of pairs of photo-detectors, each photo-detector of a pair being positioned behind either an infrared transparent strip or an infrared opaque strip with the outputs of said pair of photo-detectors being connected to a differential amplifier to measure the amount of rain accumulating on the windshield. This optical detector is more complicated, expensive and bulky. Also, it suffers from the problem of ambient light because changes in ambient light would effect the output signals of both photo-detectors of each pair. Finally, there is no way of differentiating from the light detection of raindrops on the outside surface of the windshield and the detection of fog on the inner surface of the windshield.

The optical detection method and apparatus of the present invention has several advantages over the above-discussed prior art, including the ability to monitor a much larger area of rainfall on the windshield so that the output signal of the photo-detector is more accurate in measuring small accumulations of randomly located droplets. In addition, by employing a mask to block light from being directly transmitted from the light source to the photo-detector and by employing light refraction from the raindrops to redirect the light to the photo-detector, the output signal of the photo-detector increases with increasing amounts of rain to provide more sensitive detection at the onset of rain. Also, the photo detection method and apparatus of the present invention is capable of detecting small amounts of rain in the presence of high ambient light and is not effected by changes in ambient light. The optical detection method and apparatus of the present invention also eliminates errors in the photo-detector output signal due to external factors unrelated to moisture, such as changes in temperature and aging of the LED light sources and photo-detector, power supply voltage variations or changes in ambient light by employing negative feedback through a reference light source. This reference light source sets the bias of the photo-detector to an operating point of high sensitivity to infrared light, and cancels any changes in the photo-detector output signal due to these external factors by negative feedback from the output of a tuned amplifier connected to the photo-detector transistor through a feedback circuit to the reference light source.

SUMMARY OF THE INVENTION

It is therefore one object of the present invention to provide an improved moisture detection method and apparatus of high accuracy and sensitivity in which water droplets on a window are detected by optical detection using light refraction in the droplets.

Another object of the present invention is to provide such a moisture detection method and apparatus of high sensitivity in which a light masking device is positioned in front of a photo-detector to prevent its direct irradiation by a light beam which is refracted by such water droplets to the light detector to produce a measurement output signal that increases in amplitude with increasing amounts of moisture to measure the amount of moisture accumulation on the window.

A further object of the invention is to provide such a moisture detection method and apparatus using light refraction of a first light beam for measuring the presence of rain or other water droplets on the outer surface of a window and which employs a second light beam for reflecting light off the inner surface of such window to the same photo-detector in order to detect fog on such inner surface and distinguishes between rain and fog measurements by selectively switching between such first and second light beams.

An additional object of the present invention is to provide such an improved moisture detection method and apparatus in which the same photo-detector is used to detect the first light beam and the second light beam for measuring raindrops and fog in an efficient and accurate manner.

Still another object of the invention is to provide such a moisture detection method and apparatus in which the area of the first light beam which strikes the window for detection of water droplets on the window is greatly increased in size to provide a more accurate raindrop accumulation measurement signal.

A still further object of the invention is to provide such a moisture detection method and apparatus in which a third light source is employed to provide a reference light beam for irradiating the photo-detector directly in order to bias the photo-detector at a proper operating point of high sensitivity to such light and whose bias current supply circuit is connected in a negative feedback path from the output of the photo-detector amplifier to the third light source to cancel changes in the output signal due to external factors including temperature changes and aging of the light source or photo-detector, supply voltage variations, and ambient light changes.

A still additional object of the invention is to provide such a moisture detection method and apparatus in which the first and second light sources are connected to an oscillator for pulsing such light sources to produce a pulsed output signal of the photo-detector and for amplifying such output signals with a narrowband amplifier having a tank circuit which is tuned to the oscillation frequency to reject other potentially interfering error signals which might be produced by the photo-detector.

BRIEF DESCRIPTION OF THE DRAWINGS

Other objects and advantages of the present invention will be apparent from the following detailed description of certain preferred embodiments thereof and from the attached drawings of which.

DETAILED DESCRIPTION OF THE PREFERRED EMBODIMENTS OF THE INVENTION

Figure 1:
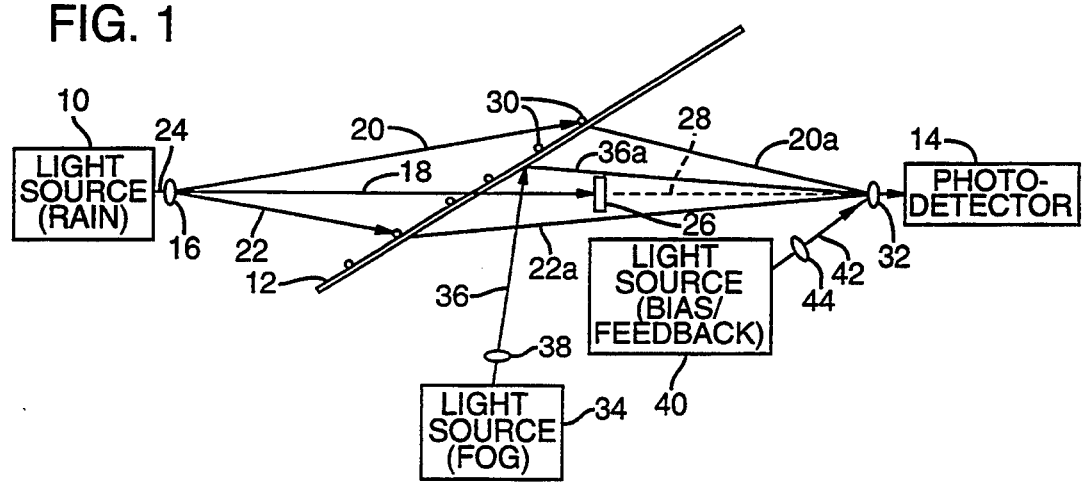
FIG. 1 is a diagram of one embodiment of a moisture detection system using the method and apparatus of the present invention suitable for detecting water droplets on the outer surface of the window by refraction of a first light beam with such droplets and for detecting fog on the inner surface of the window by reflection of a second light beam from such inner surface.

As shown in FIG. 1, one embodiment of the moisture measurement system of the present invention includes a first light source 10 positioned outside a light transparent window 12 such as the windshield of an automobile or other vehicle. The first light source 10 may be mounted under or on top of the automobile hood and spaced from a photo-electric detector 14 mounted inside of such window. A lens 16 in front of the first light source focuses the light into a first light beam having a central axis 18 and a conical shape such light beam being defined by an upper ray 20 and a lower ray 22 and intersecting the window over a large area of measurement. In this system the central axis 18 of the first light beam is aligned with the photo-detector 14 which may be a photo-transistor.

The first light source 10 is preferably a light emitting diode (LED) which when energized emits a narrow beam of infrared light 24 that passes through the lens 16 and is focused by such lens into the first light beam bounded by outer light rays 20, 22. While the light beam may be of visible light it is preferably of infrared light to avoid distraction of the vehicle driver.

In the embodiment of FIG. 1 a light opaque masking device 26, such as a metal plate, is provided in front of photo-detector 14 and on the axis 18 of the light beam to prevent the first light beam from directly irradiating the photo-detector. Thus, the central viewing axis 28 of the detector 14 through its lens 32 is aligned with the beam axis 18 along a common axis and the mask 26 is positioned across this common axis so that in absence of any water droplets upon the window 12 the photo-detector 14 does not receive the first light beam and produces substantially no output signal. However, when a plurality of water droplets 30 accumulate on the outer surface of the window 12 such water droplets refract the first light beam and cause a portion of it to be redirected to the photo-detector 14. As a result, an output signal is produced by the photo-detector whose collector current amplitude is a measurement of the amount of water droplets accumulated on the outer surface of the window. The moisture measurement value corresponds to both the number of water droplets and the area or size of such water droplets within the measurement area on such window. Thus, the upper beam limit ray 20 is refracted downward by the water droplet and redirected as refracted light ray 20A. Similarly, the lower beam limit ray 22 is refracted upward by a water droplet and redirected as refracted light ray 22A. Both of the refracted rays 20A and 22A are focused by a lens 32 to the photo-detector 14.

A second light source 34 is provided inside the window to detect fog or other moisture on the inner surface of the window 12. Thus, the second light source 34 may be another light emitting diode (LED) which emits infrared light to produce a second beam 36 that is focused by a lens 38 on the inner surface of the window. This second light beam is normally reflected off the inner surface of the window 12 as reflected beam 36A directly to the photo-detector 14 to produce a fog measurement output signal. When fog or other moisture is present on the inner surface of the window 12 a portion of the second light beam 36 is scattered and diffused by the moisture so that such portion is no longer reflected to the photo-detector 14. As a result, the fog measurement signal produced by the photo-detector 14 decreases in amplitude with greater accumulations of fog on the inner surface of the windshield. It should be noted that the second light source 34 is switched on at different times than the first light source by an electronic switch circuit in order to distinguish the fog measurement signal from the rain measurement signal produced by the photo-detector 14 in a manner hereafter described with respect to FIG. 6.

A third light source 40, such as an infrared LED, emits a third light beam 42 which acts as a reference light beam and is transmitted through a lens 44 directly to the photo-detector 14 in order to bias the photo-detector at a preferred operating point on its characteristic curve where it is of high sensitivity to infrared or other light emitted by sources 10 and 34. In addition, the third light source 40 may provide an optical negative feedback connection for a circuit (not shown) from a photo-detector output amplifier (not shown) to the photo-detector in a manner hereafter described with respect to the circuit of FIG. 6 in order to eliminate any changes in the measurement output signals of such photo-detector due to external factors such as temperature changes, aging of the light sources or photo-transistor, variations in the power supply voltage, and ambient light changes.

Figure 2:
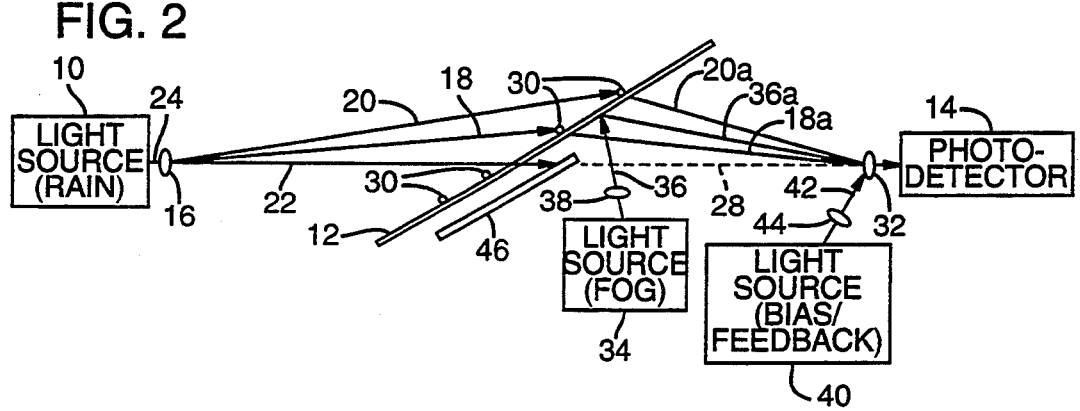
FIG. 2 is a schematic diagram of a second embodiment of the moisture detector system of the present invention in which the mask used in FIG. 1 for preventing light from being transmitted directly to the photo-detector from the first light source used for detecting water droplets is changed to a horizon-type mask which blocks the lower portion of the first light beam.

As shown in FIG. 2, a second embodiment of the moisture detection system of the present invention differs from that of FIG. 1 by employing a horizon-type mask 46 which blocks the lower portion of the first light beam 20, 22. The central viewing axis 28 of the photo-detector 14 and its associated lens 32 is not in alignment with the center axis 18 of the first light beam but is blocked by the mask 46 so that substantially none of the first light beam directly irradiates the photo-detector. However, when raindrops 30 accumulate on the outer surface of the window 12 they refract the light beam so that the upper periphery ray 20 is refracted downward as ray 20A to the photo-detector while the central axis ray 18 of the first light beam is also refracted down as refracted ray 18A to such photo-detector thereby causing an increase in the amplitude of the rain measurement output signal of the photo-detector as a measurement of the amount of raindrop accumulation on the window. As a result of upwardly inclining the center axis 18 of the first light beam so that it is not in alignment with the central viewing axis 28, its bright center region is used to measure the rain droplets which refract such light beam and redirect the refracted beam ray 18A to the photo-detector. This improves the sensitivity of the photo-detector to detecting raindrop accumulation. Other than these changes, the second embodiment of FIG. 2 is similar to that of FIG. 1 and the same reference numerals have been used in FIG. 2 to designate like parts.

Figure 3:
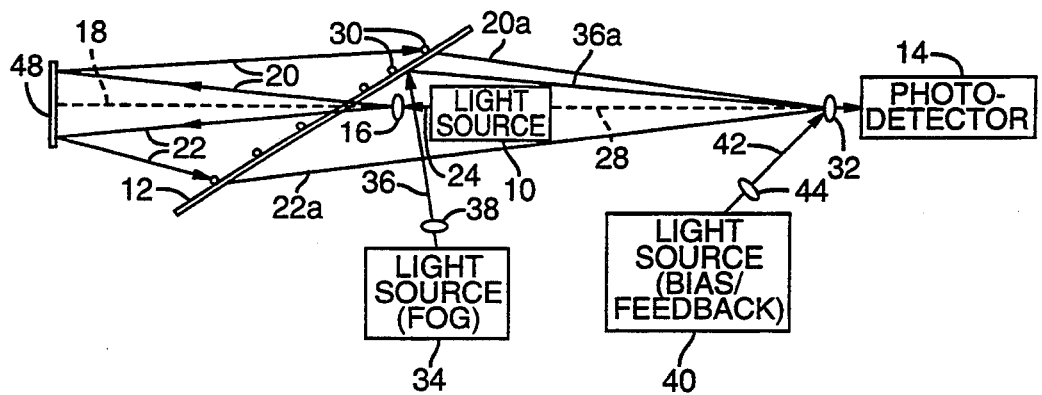
FIG. 3 is a schematic diagram of a third embodiment of the moisture detection system of the present invention which the first light source for measuring the accumulation raindrops on the outer surface of the windshield is moved to a position inside the window and is directed so that its light beam is reflected off of an external mirror positioned outside of the window before striking the water droplets and being refracted by such droplets to the photo-detector, such internal light source acting as the masking device to prevent light from such first light source from reaching the photo-detector directly without being refracted.

As shown in FIG. 3 a third embodiment of the moisture detection system of the present invention differs from that of FIG. 1 by positioning the first light source 10 and its associated lens 16 on the inside of the window 12 and adding an external mirror 48 positioned outside of the window. As a result, the first light beam 20, 22 emitted by the first light source is focused by lens 16 and transmitted through the window to the mirror 48 which reflects the first light beam back through the window so that such beam is refracted to the photo-detector 14 through its associated lens 32 when rain droplets 30 are present on the outer surface of the window. However, when no raindrops are present on the outer surface of window 12 the boundary rays 20A, 22B of the first light beam are not redirected to the photo-detector but instead are redirected so that they do not reach the photo-detector. It should be noted that in FIG. 3 the light beam passes through the window twice and is therefore attenuated more than that of FIG. 1 so that this system is not as sensitive as FIG. 1. Also in FIG. 3 the first light source 10 functions as a masking device in front of the photo-detector 14 thereby replacing the mask 26 of FIG. 1 and blocking the central viewing axis 28 of the photo-detector from directly receiving any unrefracted light from the first light source. The second light source 34 and the third light source 40 function in a similar manner in FIG. 3 to their corresponding elements in FIG. 1 and will not be described further. It should be noted that each of the three light sources 10, 34, 40 in all of the embodiments of FIGS. 1-3 are preferably light emitting diodes (LED) which emit light of the same wavelength, preferably infrared. Also, the photo-detector 14 is preferably a photo-transistor which is sensitive to infrared light.

Figure 5:
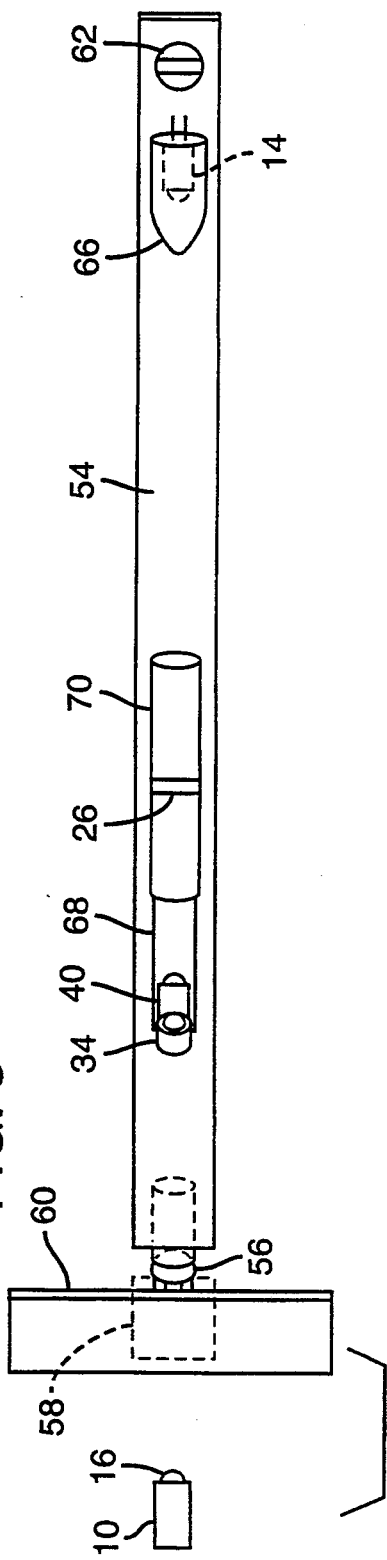
FIG. 5 is a plan view of the moisture measurement apparatus of FIG. 4.
Figure 4:
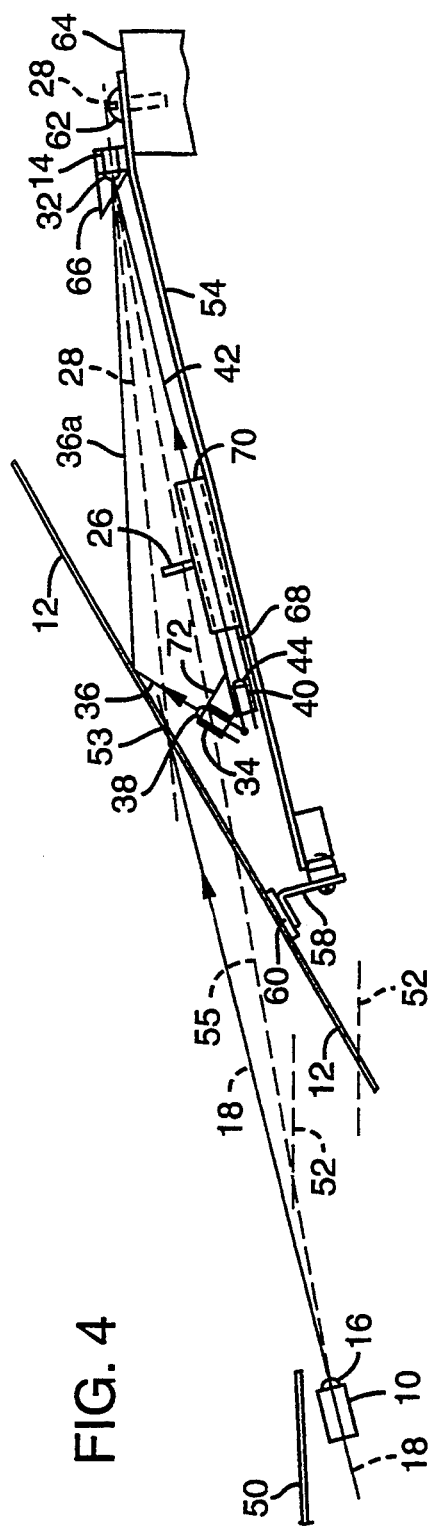
FIG. 4 is a side view of the preferred embodiment of the moisture measurement apparatus of the present invention used in a measurement system in accordance with a modification of the system of FIG. 1.

A preferred embodiment of the moisture detection apparatus of the present invention is shown in FIGS. 4 and 5 which provides a modified version of the optical detection system shown in the schematic diagram of FIG. 1. The apparatus includes first infrared light source LED 10 and associated lens 16, second infrared light source LED 34 and associated lens 38, an infrared photo-detector transistor 14 and associated lens 32, and third infrared light source LED 40 and associated lens 44. These three light sources and the photo-detector and their lenses are all supported in a similar manner to FIG. 1 to be properly positioned with respect to the window 12 which may be the windshield of an automobile or other vehicle. The first light source 10 and its lens 16 are supported on top of or beneath a hood 50 of the automobile so that the central axis 18 of the first light beam is inclined at an angle of about 13° to a horizontal reference plane 52 and intersects the windshield at point 53 but is not in alignment with the central viewing axis 28 of the photo-detector 14. Instead, unlike FIG. 1 only a lower portion of the first beam, not the center axis 18, is blocked by the mask 26 to prevent such lower portion of the first light beam from being directly transmitted to the photo-detector. A construction line 55 extending from the center of mask 26 to the first light source is at an angle of 10° with respect to the horizontal reference plane 52 and at an angle of 3° with respect to central axis 18. As a result the central axis 18 of the first light beam and its corresponding bright center pass above the mask 26 and is refracted to the photo-transistor 14 by water droplets on the outer surface of the windshield 12 to measure the accumulation of raindrops with greater sensitivity.

The windshield 12 forms an angle of approximately 30° with the horizontal reference plane 52. The center viewing axis 28 of the viewing field of the photo-transistor 14 and its associated lens 32 intersects the center axis 18 of the first beam on the outer surface of the windshield 12 at point 53. Viewing axis 28 makes an angle of 4° with the construction line 55 through the first light source 10, such angle extending above such line. The center axis of the third light beam 42 also makes an angle of about 4° with respect to the construction line 55, such angle extending below such line, and intersects the center of the lens 32 of the photo-transistor. The second light source 34 emits the second light beam 36 which forms an angle of incidence of 28° with respect to the inner surface of the windshield 12 and the reflected second beam 36A forms an angle of reflection of 28° with such inner surface of the windshield as it is reflected to the photo-transistor. Also, the axis 36 of the second light beam forms an angle of 44° with respect to the axis 42 of the second light beam.

The second light source 34 and the third light source 40 are both mounted on a metal support plate 54 which is connected by a swivel joint 56 at one end of such plate to an L-shaped support bracket 58 welded to a flat support plate 60 which may be cemented to the bottom of the windshield. The opposite end of the support plate 54 is secured by a screw 62 to a suitable support member 64 fixed to the upper surface of the dashboard of the automobile. The photo-detector 14 and its associated lens 32 are secured to the upper surface of the opposite end of support plate 50 within a tubular housing 66 welded to such plate and having an over-hanging hood which shields the photo-detector from ambient light sources. The third light source 40 is mounted within a first tubular member 68 which extends within a second tubular member 70 fixed to plate 54. The mask 26 is mounted on the top of the tubular member 70 which is of the proper inner diameter to receive the first tubular member 68 and to hold it in a sliding fit enable the third light beam of light source 40 to be transmitted therethrough to the photo-detector. The second light source 34 is fixed by a bracket 72 welded to the top of the first tubular member 68 to enable alignment of the center axis of the reflected second beam 36A with the photo-detector 14 by pivoting the first tubular member within the second fixed tubular member 70.

In the preferred embodiment of FIGS. 4 and 5 the first light source 10 is spaced a distance of about 6-⅜" from the windshield 12 at intersection point 53 along its center axis 18. The photo-detector 14 is spaced a distance of about 5-7/16" along its central viewing axis 28 from the windshield at the intersection point 53. The third light source 40 is spaced along axis 42 a distance of 4-15/16" from the lens 32 of photo-detector 14. It should be noted that the cathode leads of the second light source 34 and the third light source 40 may each have one terminal connected together to provide thermal coupling for temperature compensation.

Figure 6:
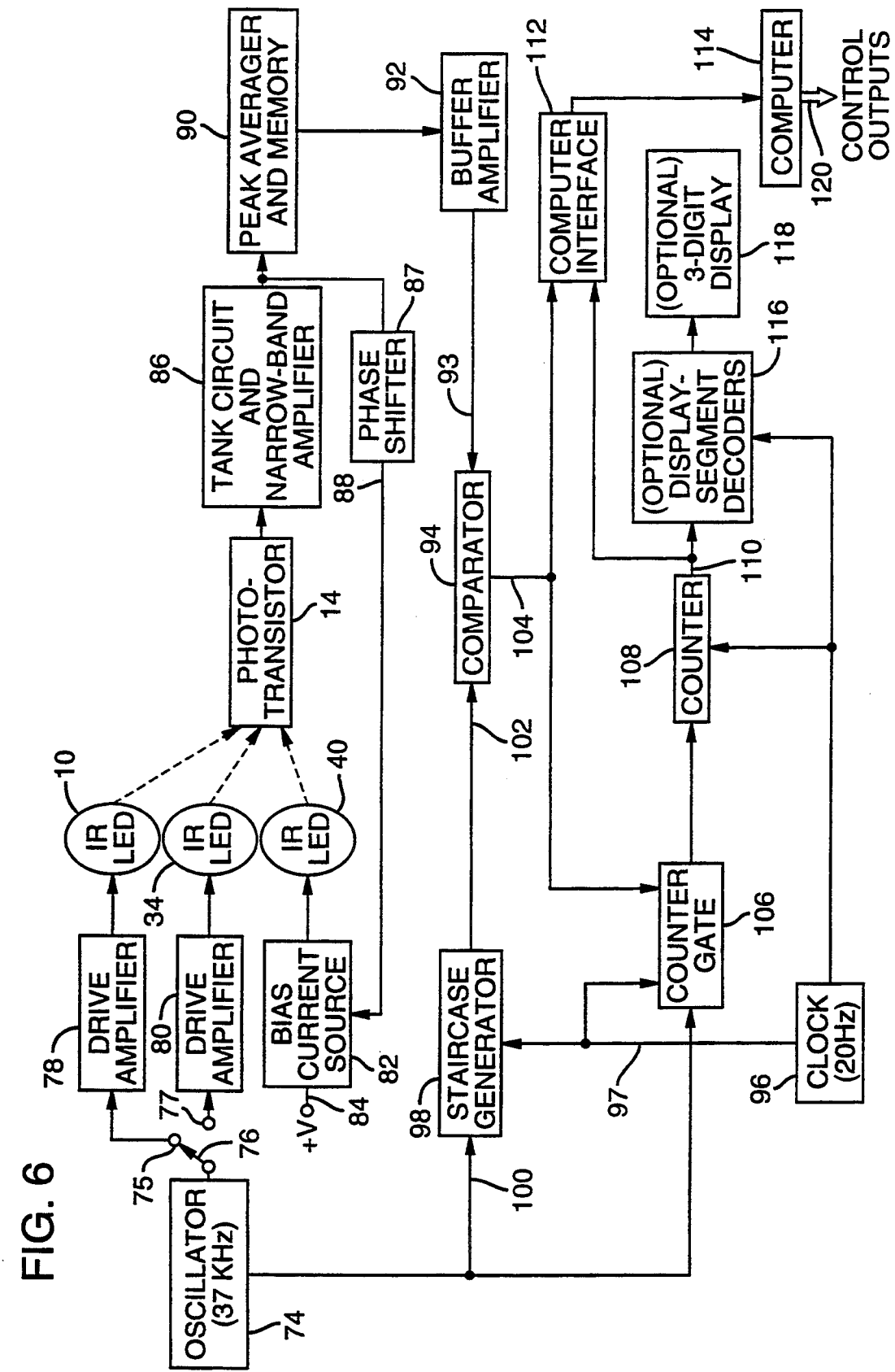
FIG. 6 is a block diagram of the electrical circuit used for the moisture measurement systems of FIGS. 1-4.

A moisture detection measurement circuit in accordance with the present invention is shown in FIG. 6 and includes an oscillator 74 which produces a square wave output signal having a frequency of approximately 37 Kilohertz. The oscillator output signal is supplied through an electronic switch 76 having two output terminals 75 and 77 connected respectively to the inputs of a pair of current drive amplifiers 78 and 80 which drive the first light source 10 and the second light source 34, respectively. Thus, the output signal of the oscillator 74 is applied to a selected one of the driver amplifiers 78 and 80 in accordance with the position of the switch 76 so that one of the light sources 10 and 34 is pulsed at a time to measure rain or fog by the same photo-detector 14 at different times. In addition, a bias current source 82 is connected to the third light source 40 and such current source is connected to a source of DC bias voltage 84 which biases the third light source normally on. The third light source 40 normally biases the photo-detector transistor 14 to its proper operating point for high sensitivity to infrared light. The output of the photo-detector 14 which may be a photo-transistor, is connected to a tuned amplifier circuit 86 which includes an RC tank circuit tuned to the 37 Kilohertz frequency of the oscillator 74. The sine wave output signal of the tuned amplifier 86 is transmitted through an RC phase shifter circuit 87 forming part of a negative feedback circuit 88 which is connected from the output of amplifier 86 to the bias current source 82 to amplitude modulate the third light source with a negative feedback sine wave signal. Also, the third light source 40 may be thermally coupled to the second light source 34 such as by connecting their cathode leads together for thermal compensation. As a result of this negative feedback, any external changes in the photo-transistor output signals due to power supply variations, temperature changes or aging of the light sources 10 and 34 and the photo-transistor and changes in ambient light will be cancelled by the negative feedback signal. In addition, the drive amplifier 78 or 80, the light sources 10 or 34 and 40, the photo-transistor 14, tuned amplifier 86 and the negative feedback circuit 82, 87, 88 in effect form an optical operational amplifier whose gain is determined by the values of the passive circuit elements including the emitter resistor of the drive amplifier transistor 78 and the resistors 140, 142 and capacitor 144 of the phase shifter 87 in the feedback path 88 for better overall gain stability.

Of course, the tuned amplifier and its associated tank circuit change the square wave signal pulses produced by the photo-transistor 14 in response to the light pulses of light sources 10 and 34 into a sine wave voltage which is amplified. This amplified sine wave is then peak detected and stored in a peak averager and memory circuit 90. Two separate memories are employed for storing the rain measurement signal, respectively, and the fog measurement signal and they are selectively connected by an electronic switch (not shown) to the output of such circuit. The analog output signal of the peak averager and memory circuit 90 is transmitted through a buffer amplifier 92 to one input 93 of a voltage comparator 94.

A clock pulse generator 96 producing clock pulses having a frequency of approximately 20 Hertz is connected at its output 97 to a start input of a staircase voltage generator 98 in order to enable such staircase generator to start to produce a stair-step voltage which increases one step for each output pulse of the oscillator 74 whose output is also connected to the staircase generator at a step input terminal 100. The stair-step voltage generated at output terminal 102 of the staircase generator is connected to a second input of the voltage comparator 94 so that when such stair-step voltage exceeds the averaged peak measurement analog voltage at the first input 93 of the comparator such comparator switches to produce an output pulse at comparator output 104.

As stated the start input terminal of the gate 106 is connected to the start output 97 of the clock 96 which starts the counter gate and the staircase generator at the same time. The output pulse of the comparator 94 is fed to the stop input terminal of a counter gate 106 to turn off such gate. As a result, counter gate 106 transmits output pulses of the oscillator 74 through such gate to the counter 108 for counting such oscillator pulses to produce a digital output measurement signal at the output 110 of such counter which corresponds to the measurement of the detected amount of rain or fog which has accumulated on the windshield of the automobile. This digital measurement output signal at output 110 is connected through a computer interface circuit 112 to a conventional digital computer, such as a microprocessor which uses the measurement value to control the operation of moisture removal devices. A result ready signal is applied by the output terminal 104 of the comparator 94 to the computer interface 112 to enable it to process the digital measurement signal produced at the output 110 of the counter.

Alternatively, for moisture measurement in a non-automobile application the digital output signal of the counter may be transmitted from output 110 to a display segment decoder circuit 116 which decodes the digital signal and applies a corresponding measurement signal to a three digit display circuit 118 which displays the value of the moisture measurement. The clock 96 produces a reset signal which is applied to the counter 108 to reset the counter to zero at the end of a measurement and a blanking signal to the display segment decoder 116 to blank such decoder between measurements.

It should be noted that the water accumulation measurement signal at the output of the counter 108 is a measure of both the number and size of the water droplets detected by the first light source 10 and the photo-transistor 14 and therefore represents the total amount of water accumulated on the outer surface of the windshield. Also the value of this measurement signal increases with an increasing amount of water droplets on the outer surface of such windshield. However, when fog is measured on the inner surface of the windshield by the second light source 34 and the photo-transistor 14 the output signal of the counter 108 decreases with increasing amount of fog. This difference between the rain and fog signals is taken into account when the signals are processed by the computer 114 for a proper display of the measurement values of rain and fog and proper operation of moisture removal devices by control signals at the control outputs 120 of the computer.

Also the electronic switch 76 for switching the output of the oscillator 74 to either the input 75 of the driver amplifier 78 of the first light source 10 or the input 77 of the driver amplifier 80 of the second light source 34, is controlled by a control signal generated by a separate control logic circuit or by the computer at one of the control outputs 120 for alternately taking measurements of the rain droplet accumulation on the outer surface of the windshield or fog measurements of the amount of fog accumulation on the inner surface of the windshield. The computer output control signal is employed to operate various visibility improving devices such as windshield wipers which may be turned on and whose speed may be varied by the computer depending upon the raindrop accumulation. Also electrical heaters and air blowers may be operated to remove the fog from the inner surface of the windshield of the automobile. In addition, the computer output control signal can also be used to control motors for closing windows such as the sunroof window of an automobile or raising the convertible top of a convertible-type automobile.

Figure 7:
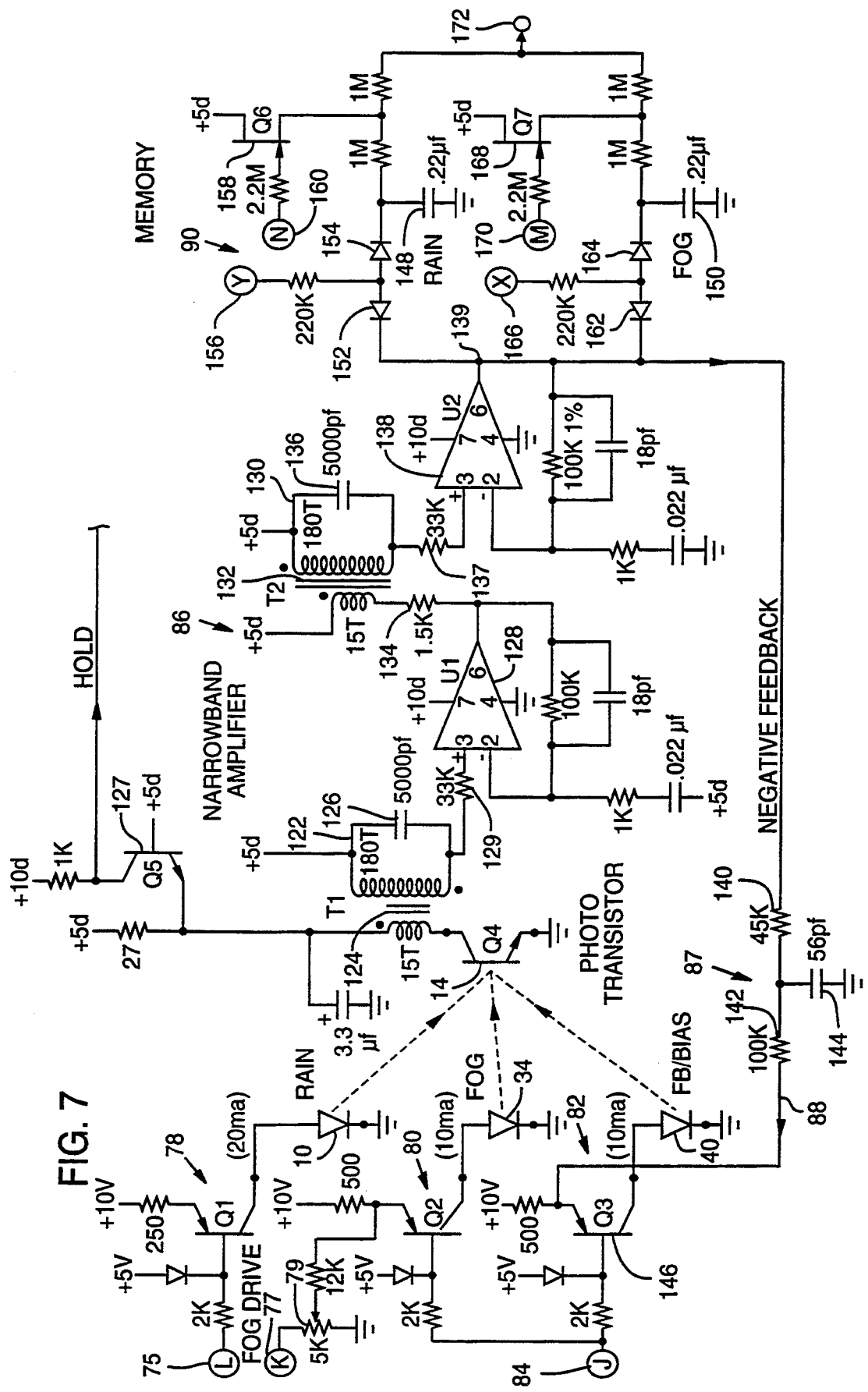
FIG. 7 is an electrical circuit of a portion of the block diagram of FIG. 6.

As shown in FIG. 7, the tuned narrowband amplifier circuit 86 has two amplifier stages including a first stage having a first LC tank circuit 122 including a first transformer 124 with its primary winding connected in series with the collector of the photo-detector transistor 14 and having its secondary winding connected in parallel with a capacitor 126 of the proper value so that such tank circuit is tuned to the 37 Kilohertz frequency of the oscillator 74. It should be noted that a switching transistor 127 is connected to the upper end of the primary winding of transformer 124 to prevent the photo-transistor from producing a measurement signal when such switching transistor is switched on to produce a hold signal which disables the measurement clock 96, such as when a high brightness ambient light drives the photo-transistor into saturation. The output of the tank circuit 122 is connected to the positive input of a first stage amplifier 128 through a coupling resistor 129. The oscillator through the electronic switch 76 selectively applies the oscillator pulses to inputs 75 or 77 of the driver amplifiers 78 or 80 for the first and second light emitting diodes 10, or 34, respectively. It should be noted that the input 77 is connected through a variable resistance potentiometer 79 to the emitter of the driver amplifier transistor 80 in order to adjust the amplitude of the fog drive input signal, and the base of such transistor is connected to the DC bias voltage at terminal 84. The DC bias voltage sources indicated as "$+5d$" and "$+10d$" are LC decoupled DC voltage sources of $+5$ volts and $+10$ volts.

The second stage of the tuned amplifier 86 includes a second tank circuit 130 with a second transformer 132 having its primary winding connected in series with a load resistor 134 to the output of amplifier 128. The secondary winding of transformer 132 is connected in parallel with a capacitor 136 of the proper value to tune the second tank circuit 130 to the same 37 Kilohertz frequency of the oscillator. The output of the second tank circuit is connected through a coupling resistor 137 to the positive input of a second amplifier 138 which produces an output signal voltage at its output terminal 139.

A negative feedback circuit is connected from the output 139 of the second amplifier 138 through an RC phase shift circuit 87 including an input coupling resistor 140 an output coupling resistor 142 and a shunt capacitor 144 connected from a point between such resistors and ground.

The negative feedback signal is applied to the emitter of a transistor 146 in the current supply circuit 82 which supplies bias current for the third light source 40. The base of transistor 146 is connected to a source of DC bias voltage at terminal 84 which normally biases such transistor conducting to cause current to flow from the collector of such transistor through the light emitting diode (LED) 40 to normally bias such LED on so that it emits the third light beam. This third light beam is directed onto the photo-transistor 14 in order to optically bias such photo-transistor at an operating point on its characteristic curve of high sensitivity to infrared light. It should be noted that the driver amplifiers 78, 80 of the first light source 10 and second light source 34 are normally biased off and are switched into an on condition by the square wave oscillator signals applied to input terminal 75 and 77 by the electronic switch 76 as shown in FIG. 6. Thus, the light sources 10 and 34 are pulsed on and off by the oscillator signal square wave pulses to produce a corresponding pulsed output signal on the collector of the photo-transistor 14 which is then changed into a sine wave by the tuned tank circuits 122, 130.

The negative feedback signal from the third light emitting diode 40 is coupled by photo-transistor 14 and the primary winding of transformer 124 to stimulate tank circuit 122 in a manner which is 180° out of phase from the stimulation produced in tank circuit 122 by the input signal from the first or second light emitting diode 10 or 34. As a result, the tank circuit voltage is reduced to a small fraction of what it would otherwise be with no feedback signal applied. The effects of sensitivity changes in the light emitting diodes or photo-transistor caused by temperature changes, aging, power supply variations or changes in ambient light are also reduced accordingly. Using tank circuit 122 as the starting point, the voltage produced by the input signal from the first or second light emitting diode 10 or 34 is phase shifted a total of 22° in the circuits associated with amplifier 128, transformer 132, tank circuit 130 and amplifier 138. Phase shifted circuit 87 adds 68° while transistor 82, light emitting diode 40 and photo-transistor 14 do not add appreciable phase shift. The normal phase difference at resonance between the inductor current and the capacitor voltage in tank circuit 122 adds another 90° for a total phase shift around the loop of 180°.

The sine wave output signal of the second amplifier stage 138 of the narrowband amplifier 86 is transmitted from output terminal 139 to the input of the peak averager and memory circuit 90 where it is averaged and stored as a DC analog voltage in either a rain memory capacitor 148 or a fog memory capacitor 150. A first charging gate including a first pair of anode connected gating diodes 152, 154 is connected between the output of amplifier 138 and the upper plate of rain memory capacitor 148 to charge such capacitor to the peak amplitude of the rain measurement output signal only when such gate is rendered conducting by a computer control square wave gate signal applied to a gate terminal 156 connected to the common connection of the anodes of such diodes. Switching transistor 158 is connected as a shunt to the +5 volts DC supply between rain memory capacitor 148 and the memory output 172. During a rain measurement, a square wave signal applied to control terminal 160 connected to the gate of field effect transistor 158 renders it non-conducting such that the rain measurement signal stored in rain memory capacitor 148 reaches the memory output 172. During a fog measurement, however, transistor 158 is rendered conducting thus inhibiting the stored rain measurement signal from reaching the memory output 172. A similar charge gate 162, 164 and switching transistor 168 are provided for the fog memory capacitor 150. Thus, the fog memory capacitor 158 is connected through a second charging gate formed by a pair of diodes 162 and 164 having their common anode connection connected to a gate control input 166 for rendering such gate conductive to charge the fog memory capacitor 150 from the output of the amplifier 138 through such gate. Switching transistor 168 is connected as a shunt to the +5 volts DC supply between fog memory capacitor 150 and the memory output 172. During a fog measurement, a square wave signal applied to control terminal 170 connected to the gate of field effect transistor 168 renders it non-conducting such that the fog measurement signal stored in fog memory capacitor 150 reaches the memory output 172. During a rain measurement, however, transistor 168 is rendered conducting thus inhibiting the stored fog measurement signal from reaching the memory output 172. It should be noted that the charging control signals on terminals 156 and 166 are square waves which are phase inverted with respect to each other so that gate 152, 154 is open when gate 162, 164 is closed and vice versa. However, there is a time delay between the termination of the gate on signal at terminal 156 and the start of the gate on signal at terminal 166. During such time delay a charge voltage on the rain memory capacitor 148 is transmitted through the buffer amplifier 92 to the comparator for operating the counter gate 106 to cause the counter 108 to count the rain measurement in FIG. 6. The rain measurement signal at counter output 110 is subsequently displayed after the count is completed and while the fog signal is charging fog memory capacitor 150.

The disabling control signals on terminals 160 and 170 are phase inverted with respect to each other so that switch 158 is on while switch 168 is off and vice versa. As a result, depending upon whether switches 158 and 168 are on or off either the rain measurement signal stored on memory capacitor 148 or the fog measurement signal stored on memory capacitor 150 is supplied from the output 172 of the memory through the buffer amplifier 92 to the comparator 93 of FIG. 6. In this way, the moisture detection system produces with light sources 10 and 34 at different times the two output measurement signals at the output 110 of the counter 108 including a rain measure signal corresponding to the raindrop accumulation on the outer surface of the windshield and a fog measurement signal corresponding to the fog accumulation on the inner surface of such windshield.

It should be noted that the charge control signals applied to control terminals 156, 166 and the disabling control signals applied to control terminals 160, 170 are all produced by the computer and supplied from different ones of its control output terminals 120 at appropriate times as is the control signal for operating the electronic switch 76 for selecting light sources 10 and 34 which determines whether rain or fog measurements are to be taken.

It should be noted that the above-described preferred embodiments of the present invention are merely illustrative of the present invention. Many changes may be made in such preferred embodiments which will be obvious to those having ordinary skill in the art. Therefore, the scope of the present invention should only be determined by the following claims.

I claim:

1. An optical droplet detector apparatus for determining the degree of vision impairment through a window due to an accumulation of water or other precipitation on the window comprising:

a first light source for illuminating water droplets on said window with a first light beam transmitted through said window to the inside of said window;

a photo-detector located inside said window; and a masking device positioned in front of said photo-detector to effectively block the direct transmission of light rays from said first light source to said photo-detector, but allowing said photo-detector to receive light rays from said first source which have been refracted by droplets on said window for the purpose of determining the amount of water on said window so that the output signal of said photo-detector increases with an increase in water droplets on said window.

2. Apparatus in accordance with claim 1 wherein the first light beam detects rain droplets on the outside surface of the window, the masking device is positioned between the first light source and the photo-detector and which also includes a second light source positioned inside said window to produce a second light beam for detecting fog on the inside surface of the window which reflects off the inside surface to said photo-detector for the purpose of determining the degree of fog accumulation on said inside surface, said first and second light sources emitting infrared light.

3. Apparatus in accordance with claim 1 which also includes a third light source positioned inside said window with its beam directly aimed at said photo-detector for the purpose of optically driving said photo-detector to its bias operating point and for providing an optical feedback signal to said photo-detector.

4. Apparatus in accordance with claim 3, further comprising a drive circuit for providing pulsed drive current to said first light source for water accumulation measurements and another drive circuit connected to said third light source for gain stabilization, and an output circuit for amplifying the pulsating output current produced by the photo-detector.

5. Apparatus in accordance with claim 4, wherein said output circuit includes a narrowband amplifier and tank circuit closely tuned to the frequency of the pulsed drive current for the purpose of rejecting other, potentially interfering currents produced by said photo-detector.

6. Apparatus in accordance with claim 4, wherein a feedback circuit is connected from said output circuit to the drive circuit for the third light source to provide an out-of-phase, negative feedback signal to modulate said third light source to provide an optical operational amplifier circuit for the purpose of overall gain stabilization.

7. Apparatus in accordance with claim 1, further comprising detector circuit means connected to the output of the photo-detector for peak detection, averaging and temporary storage of the photo-detector output signals to produce output signal data pertaining to visibility impairment of said window, reducing the effects of noise and unwanted signals in the data, and temporarily storing the data for subsequent analog-to-digital conversion or threshold comparison.

8. Apparatus in accordance with claim 2, further comprising an analog-to-digital converter for converting the analog output signal of the photo-detector pertaining to visibility impairment to a pair of digital output signal related to measurements for rain and fog, respectively, and computer interface circuits to interface said digital output signal to a microprocessor for the purpose of making threshold and state-transition decisions to control devices for restoring visibility or for closing windows.

9. Apparatus in accordance with claim 8, wherein a digital offset measurement is made of the output signals at a zero-drive-signal condition obtained when neither said first light source nor said second light source are driven for the purpose of subtracting said offset value from the output signals corresponding to each subsequent rain and fog measurement to eliminate any residual zero-offset errors from said rain and fog measurements.

10. A water droplet detector for determining the degree of vision impairment through a windshield of a vehicle due to an accumulation of water on said windshield comprising:

a first sensor incorporating a first light source and a photo-detector for the purpose of determining the degree of water accumulation on the outside surface of said windshield;

a second sensor incorporating a second light source and said photo-detector for the purpose of determining the degree of fog accumulation on the inside surface of said windshield;

a third light source for the purpose of optically driving said photo-detector to its bias operating point;

a drive circuit for providing pulsed drive current to said first light source and to said second light source;

an output circuit connected to the photo-detector including a tuned amplifier for providing narrowband amplification closely tuned to the frequency of said pulsating drive currents for the purposes of amplifying the pulsating output current produced by said photo-detector and rejecting other, potentially interfering currents produced by said photo-detector; and a feedback circuit connected from said output circuit to said third light source for providing attenuation and additional phase shift to the output signal of said output circuit to provide a negative feedback signal to modulate said third light source for the purpose of gain stabilization of said output circuit.

11. Apparatus in accordance with claim 10, further comprising a detector circuit means connected to the output circuit for peak detection, averaging and temporary storage of the output signals for producing output signal data pertaining to visibility impairment of said windshield, for reducing the effects of noise and unwanted signals in the data, and for temporarily storing the data for subsequent analog-to-digital conversion or threshold comparison.

12. Apparatus in accordance with claim 10, further comprising an analog-to-digital converter for converting the analog output signals of the output circuit pertaining to visibility impairment to a pair of digital output signals relating to measurements for rain and fog, respectively, computer interface circuits to interface said digital output signals to a microprocessor for the purpose of making threshold and state-transition decisions to control devices for restoring visibility or for closing windows, and offset means for measuring the digital offset of the output signals at a zero-drive-signal condition obtained when neither said first light source nor said second light source are driven, for the purpose of subtracting said offset value from the output signals corresponding to each subsequent rain and fog measurement to eliminate any residual zero-offset errors from said rain and fog measurements.

13. Apparatus in accordance with claim 10 in which the light sources and their drive circuits together with the photo-detector and its output circuit and feedback circuit are connected as an optical operational amplifier for gain stability.

14. A method of optical detection of water or other precipitation on a window to determine the degree of vision impairment through the window due to the accumulation of water on said window, comprising the steps of:

transmitting a first light beam from a first light source through said window to the inside of said window;

detecting the first light beam with a photo-detector inside said window;

blocking the direct transmission of light rays from said first light source to said photo-detector by a light masking device; and refracting said first light beam with water droplets or other precipitation on said window to cause a portion of said first light beam to be redirected from said water droplets to said photo-detector so that the detector output signal of said photo-detector increases with an increase in water droplets on said window.

15. A method in accordance with claim 14 in which the first light beam is transmitted from a first light source outside the window and is refracted by rain droplets on the outside surface of the window, and which also includes the step of:

transmitting a second light beam from a second light source inside the window so that said second light beam is reflected off the inside surface of the window to the photo-detector for determining the amount of fog accumulation on said inside surface by decreases in the detector output signal with increases in fog on the inner surface of said window due to diffusion of the light beam by the fog.

16. A method in accordance with claim 14 which also includes the step of:

transmitting a third light beam from a third light source directly to the photo-detector to optically drive the photo-detector to its bias operating point.

17. A method in accordance with claim 15 which also includes the step of:

applying pulsed drive current selectively to the first light source and to the second light source to cause them to emit light which is pulsed at a predetermined frequency to cause the photo-detector to produce a pulsed output signal.

18. A method in accordance with claim 17 which also includes the step of:

transmitting the pulsed output signal of the photo-detector through an output circuit including a narrowband amplifier and tank circuit tuned to the frequency of the pulsed drive current.

19. A method in accordance with claim 18 which also includes the step of:

transmitting a negative feedback signal from the photo-detector output circuit to the drive circuit of the third light source.

20. A method in accordance with claim 18 which also includes the steps of:

peak detection of the analog photo-detector output signal at the output of the photo-detector output circuit;

converting the analog photo-detector output signal to a digital output signal; and processing said digital output signal with a computer to produce digital data corresponding to measurements of the amount of water on the window.

* * * * *

UNITED STATES PATENT AND TRADEMARK OFFICE
CERTIFICATE OF CORRECTION

PATENT NO. : 5,386,111  
DATED : January 31, 1995  
INVENTOR(S) : H. Allen Zimmerman It is certified that error appears in the above-indentified patent and that said Letters Patent is hereby corrected as shown below:

In the Abstract:

Line 2: "and fog" should read --and for detecting fog--;

Line 3: "surface with" should read --surface of such window with--;

Line 3: "photo-detector." should read --photo-detector is disclosed.--;

Lines 3 and 4: "The invention" should read --The optical detection method and apparatus of the invention--;

Line 6: "with droplets" should read --with such droplets--;

Line 7: "prevents light from" should read --prevents such first light beam from--;

Lines 13 and 14: "the output" should read --the fog measurement output--;

Line 15: "scatters the" should read --scatters and diffuses the--;

Line 25: "signal due" should read --signal of the photo-detector due--;

Line 26: "factors are" should read --factors such as temperature changes or aging of the light sources and photo-detector, as well as changes in the supply voltage and ambient light are--; and

UNITED STATES PATENT AND TRADEMARK OFFICE
CERTIFICATE OF CORRECTION

PATENT NO. : 5,386,111
DATED : January 31, 1995
INVENTOR(S) : H. Allen Zimmerman It is certified that error appears in the above-indentified patent and that said Letters Patent is hereby corrected as shown below:

Line 27: "errors." should read --errors in the measurement signals.--.

Signed and Sealed this

Twenty-fourth Day of October, 1995

Attest:

BRUCE LEHMAN

*Attesting Officer*            *Commissioner of Patents and Trademarks*